United States Patent
Lösch et al.

(10) Patent No.: US 8,268,942 B2
(45) Date of Patent: Sep. 18, 2012

(54) PRODUCTION OF POLYMERS BY SPRAY POLYMERIZATION

(75) Inventors: Dennis Lösch, Altrip (DE); Volker Seidl, Mannheim (DE); Uwe Stueven, Bad Soden (DE)

(73) Assignee: BASF Aktiengesellschaft

( * ) Notice: Subject to any disclaimer, the term of this patent is extended or adjusted under 35 U.S.C. 154(b) by 41 days.

(21) Appl. No.: 11/813,305

(22) PCT Filed: Jan. 14, 2006

(86) PCT No.: PCT/EP2006/000289
§ 371 (c)(1),
(2), (4) Date: Jul. 3, 2007

(87) PCT Pub. No.: WO2006/077054
PCT Pub. Date: Jul. 27, 2006

(65) Prior Publication Data
US 2008/0188821 A1 Aug. 7, 2008

(30) Foreign Application Priority Data
Jan. 18, 2005 (DE) .......................... 10 2005 002 412

(51) Int. Cl.
*C08F 20/06* (2006.01)
*C08F 20/26* (2006.01)
(52) U.S. Cl. .................. 526/88; 526/317.1; 526/320
(58) Field of Classification Search .................... 526/88, 526/317.1
See application file for complete search history.

(56) References Cited

U.S. PATENT DOCUMENTS

| | | | | |
|---|---|---|---|---|
| 5,010,150 A | * | 4/1991 | Hennig et al. | 526/88 |
| 5,059,664 A | * | 10/1991 | Yada et al. | 526/240 |
| 5,506,324 A | | 4/1996 | Gartner et al. | |
| 5,532,323 A | * | 7/1996 | Yano et al. | 525/384 |
| 5,849,816 A | * | 12/1998 | Suskind et al. | 523/201 |
| 6,150,477 A | | 11/2000 | Engelhardt et al. | |
| 7,393,908 B2 | * | 7/2008 | Heide et al. | 526/318.43 |
| 2004/0014901 A1 | * | 1/2004 | Heide et al. | 525/330.3 |
| 2006/0217508 A1 | | 9/2006 | Schmid et al. | |

FOREIGN PATENT DOCUMENTS

| | | |
|---|---|---|
| DE | 103 40 253 | 3/2005 |
| DE | 102004024437 | 12/2005 |
| EP | 0 348 180 | 12/1989 |
| EP | 0 816 383 | 1/1998 |
| JP | 01126314 | 5/1989 |
| JP | 05011446 A * | 1/1993 |
| WO | WO-96/40427 | 12/1996 |
| WO | WO-2005/030810 | 4/2005 |

OTHER PUBLICATIONS

Translation of Nagasuna et al, JP 01126314 A, Feb. 2009.*
Machine translation of Mori et al. JP 05011446A, translated on Apr. 13, 2011.*
Buchholz and Graham, "Modern Superabsorbent Polymer Technology," Wiley-VCH, pp. 97-103 (1998).
International Search Report in PCT/EP2006/000289 dated Mar. 29, 2006.

* cited by examiner

*Primary Examiner* — Mark Eashoo
*Assistant Examiner* — Nicole M Buie-Hatcher
(74) *Attorney, Agent, or Firm* — Marshall, Gerstein & Borun LLP

(57) ABSTRACT

Water-absorbing polymeric particles are produced by spray polymerization of a monomer solution in a process wherein the monomer solution is spray dispensed and at least one crosslinker accumulates in the region of the droplet surface, and are useful in hygiene articles.

6 Claims, No Drawings

PRODUCTION OF POLYMERS BY SPRAY POLYMERIZATION

CROSS-REFERENCE TO RELATED APPLICATIONS

This is the U.S. national phase application of International Application No. PCT/EP2006/000289, filed Jan. 14, 2006 which claims the benefit of German Patent Application No. 10 2005 002 412.2, filed Jan. 18, 2005.

The present invention relates to a process for producing water-absorbing polymeric particles by spray polymerization of a monomer solution, to the water-absorbing polymeric particles themselves and to hygiene articles comprising these water-absorbing polymeric particles.

Further embodiments of the present invention are discernible from the claims, the description and the examples. It will be understood that the hereinbefore mentioned and the hereinbelow still to be more particularly described features of the subject matter of the present invention are utilizable not only in the particular combination indicated but also in other combinations without departing from the realm of the invention.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products swellable in aqueous fluids, such as guar derivatives for example. Such polymers are used as products capable of absorbing aqueous solutions to produce diapers, tampons, sanitary napkins and other hygiene articles, but also as water-retaining agents in market gardening.

The properties of the water-absorbing polymer can be controlled via the degree of crosslinking. Gel strength increases and absorptive capacity decreases with increasing degree of crosslinking. Consequently, as Absorbency Under Load (AUL) increases, Centrifuge Retention Capacity (CRC) decreases (although at very high degrees of crosslinking absorbency under load decreases, too).

To improve their performance characteristics, for example Saline Flow Conductivity (SFC) in the diaper and Absorbency Under Load (AUL), water-absorbing polymeric particles are generally postcrosslinked. This increases only the degree of crosslinking of the particle surface, making it possible to decouple Absorbency Under Load (AUL) and Centrifuge Retention Capacity (CRC) to some extent at least. Postcrosslinking can be carried out in the aqueous gel phase. Preferably, however, ground and screened particles of the base polymer are surface coated with a postcrosslinker, dried and thermally postcrosslinked. Useful postcrosslinkers include compounds comprising at least two groups capable of forming covalent bonds with the carboxylate groups of the hydrophilic polymer.

Postcrosslinking is described in the monograph "Modern Superabsorbent Polymer Technology", F. L. Buchholz and A. T. Graham, Wiley-VCH, 1998, pages 97 to 103. Typically, the water-absorbing polymeric particles are wetted with the postcrosslinker and thermally postcrosslinked by the polymeric particles being heated, and concurrently dried, by means of hot air or by means of contact drying.

One disadvantage with existing processes is that the polymerization, the drying and the classifying of the base polymer and the thermal postcrosslinking have to be carried out as distinct operations.

Spray polymerization is a way to combine the polymerization and drying steps. In addition, particle size became controllable within certain limits through suitable process management.

The production of water-absorbing polymeric particles by spray polymerization is described for example in EP-A-0 348 180, WO-A-96/40427 and also prior German patent applications 10340253.5 and 102004024437.5.

But existing spray-polymerization processes still need an additional postcrosslinking step. It has proved impossible to obtain water-absorbing polymeric particles having sufficient Saline Flow Conductivity (SFC) and Absorbency Under Load (AUL) without this additional step.

The present invention therefore has for its object to provide an improved process for producing water-absorbing polymeric particles.

More particularly, a monomer solution shall be convertible in a single operation into water-absorbing polymeric particles possessing a higher degree of crosslinking in the region of the particle surface than in the particle interior.

Furthermore, a monomer solution shall be convertible in a single operation into water-absorbing polymeric particles having improved Absorbency Under Load (AUL) and high Centrifuge Retention Capacity (CRC).

We have found that this object is achieved by a process for producing water-absorbing polymeric particles by spray polymerization of a monomer solution comprising a) at least one ethylenically unsaturated acid-functional monomer, b) at least one crosslinker, c) if appropriate one or more ethylenically and/or allylically unsaturated monomers copolymerizable with the monomer a), and d) if appropriate one or more water-soluble polymers onto which the monomers a), b) and if appropriate c) can be at least partly grafted, the monomer solution being spray dispensed, wherein the at least one crosslinker b) accumulates at the droplet surface.

The accumulation rate of crosslinker b) is determined by measurements of the dynamic surface tension in the monomer solution in accordance with ASTM D3825. Gas bubbles are generated in the monomer solution and the surface tension of the gas bubbles is determined as a function of bubble life. As crosslinker b) diffuses, the surface tension (dynamic surface tension) will change until a state of equilibrium is reached (static surface tension). The time to equilibrium is a measure of how quickly crosslinker b) accumulates at the phase boundary, and is typically less than 10 seconds, preferably less than 5 seconds and more preferably less than one second. The system is considered to be at equilibrium when subsequent change amounts to less than 5% of total change.

The crosslinkers b) comprise preferably at least two free-radically polymerizable groups.

Suitable crosslinkers b) are crosslinkers comprising hydrophobic and hydrophilic groups, examples being hydrophilic crosslinkers which have been modified to be hydrophobic. Preferably, it is the hydrophilic radicals which comprise the polymerizable groups.

The starting materials for the crosslinkers b) can be polyols which themselves accumulate at the surface of spray-dispensed droplets of aqueous solution. Examples thereof are block polymers based on propylene oxide and ethylene oxide.

Preferred crosslinkers b) are crosslinkers of the general formula I

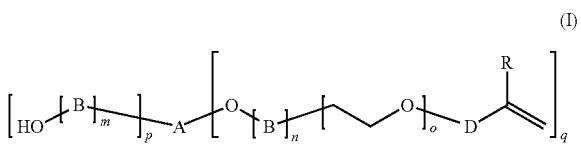

where
R represents the same or different radicals selected from the group consisting of hydrogen, methyl and ethyl,
A represents a $C_3$- to $C_{20}$-alk(p+q)yl or $C_3$- to $C_{20}$-heteroalk(p+q)yl,
B represents the same or different groups selected from

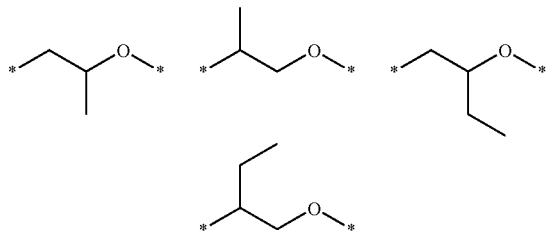

and * designates the positions of attachment,
D represents the same or different groups selected from carbonyl and methylene,
m, n and o are each an integer from 0 to 100,
p is an integer from 0 to 6, and
q is an integer from 2 to 6,
where p+q is preferably an integer from 2 to 6.

Particularly preferred crosslinkers b) are crosslinkers of the general formula I where
R represents the same or different radicals selected from the group consisting of hydrogen and methyl,
A represents a $C_3$- to $C_{10}$-alk(p+q)yl or $C_3$- to $C_{10}$-heteroalk(p+q)yl,
B represents the same or different groups selected from

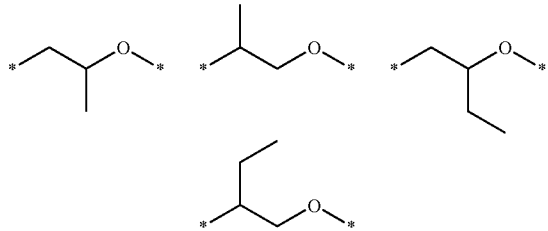

and * designates the positions of attachment,
D represents the same or different groups selected from carbonyl and methylene,
m, n and o are each an integer from 1 to 50,
p is an integer from 0 to 4, and
q is an integer from 2 to 4,
where p+q is preferably an integer from 2 to 4.

Very particularly preferred crosslinkers b) are crosslinkers of the general formula I where
R represents hydrogen,
A represents a $C_3$- to $C_6$-alk(p+q)yl or $C_3$- to $C_o$-heteroalk(p+q)yl,
B represents the same or different groups selected from

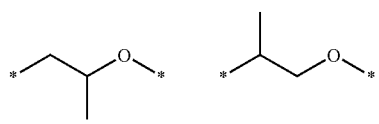

and * designates the positions of attachment,
D represents the same or different groups selected from carbonyl and methylene,
m, n and o are each an integer from 2 to 30,
p is an integer from 0 to 2, and
q is 2 or 3,
where p+q is preferably 2 or 3.

Further preferred crosslinkers b) are crosslinkers of the general formula II

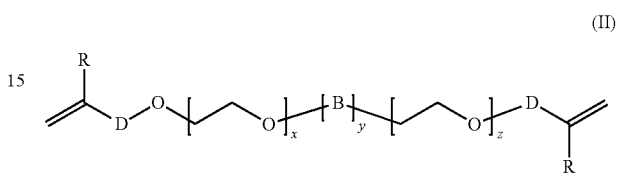

where R, B and D are each as defined above and
preferably
x and z are the same or different and each represent an integer from 0 to 100 and
y represents an integer from 1 to 200,
more preferably
x and z are the same or different and each represent an integer from 1 to 50 and
y represents an integer from 3 to 100,
and most preferably
x and z are the same or different and each represent an integer from 2 to 30 and
y represents an integer from 5 to 60.

Suitable monomers a) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Acrylic acid and methacrylic acid are particularly preferred. Acrylic acid is most preferable.

The acid groups of monomers a) are typically in a partially neutralized state, the extent of neutralization being preferably in the range from 25 to 85 mol %, more preferably in the range from 27 to 80 mol %, and even more preferably in the range from 27 to 30 mol % or from 40 to 75 mol %, for which the customary neutralizing agents can be used, preferably alkali metal hydroxides, alkali metal oxides, alkali metal carbonates or alkali metal bicarbonates and also mixtures thereof. Ammonium salts can also be used instead of alkali metal salts. Sodium and potassium are particularly preferred as alkali metals, but most preference is given to sodium hydroxide, sodium carbonate or sodium bicarbonate and also mixtures thereof. Typically, neutralization is achieved by mixing the neutralizing agent as an aqueous solution, as a melt or else preferably as a solid material into the monomer solution. For example, sodium hydroxide having a water fraction of distinctly below 50% by weight can be present as a waxy mass having a melting point above 23° C. In this case, metering as piece goods or melt at elevated temperature is possible.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

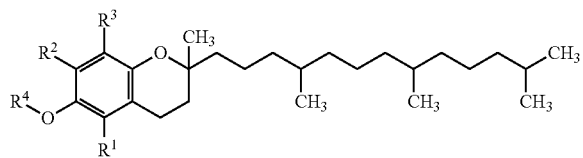

where $R^1$ is hydrogen or methyl, $R^2$ is hydrogen or methyl, $R^3$ is hydrogen or methyl and $R^4$ is hydrogen or an acyl radical of 1 to 20 carbon atoms.

Preferred $R^4$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^1=R=R=$methyl, especially racemic alpha-tocopherol. $R^1$ is more preferably hydrogen or acetyl. RRR-alpha-tocopherol is preferred in particular.

The monomer solution comprises preferably not more than 130 weight ppm, more preferably not more than 70 weight ppm, preferably not less than 30 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

Preferably, as well as the crosslinkers b), the monomer solution further comprises further crosslinkers b'). The crosslinkers b') are compounds having at least two polymerizable groups which can be free-radically interpolymerized into the polymer network. By using the crosslinkers b') in combination with the crosslinkers b) the degree of crosslinking in the region of the particle surface and the degree of crosslinking in the particle interior can be optimized independently of each other. Suitable crosslinkers b') are for example ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates as described in EP-A-0 547 847. EP-A-0 559 476, EP-A-0 632 068, WO-A-93/21237, WO-A-03/104299, WO-A-03/104300, WO-A-03/104301 and in German patent application 10331450.4, mixed acrylates which, as well as acrylate groups, comprise further ethylenically unsaturated groups, as described in German patent applications 10331456.3 and 10355401.7, or crosslinker mixtures as described for example in DE-A-195 43 368, DE-A-196 46 484, WO-A-90/15830 and WO-A-02/32962.

Useful crosslinkers b') include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triailylamine, tetraallylethylenediamine, allyl esters of phosphoric acid and also vinylphosphonic acid derivatives as described for example in EP-A-0 343 427. Useful crosslinkers b') further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention utilizes di(meth)acrylates of polyethylene glycols, the polyethylene glycol used having a molecular weight between 300 and 1000.

However, particularly advantageous crosslinkers b') are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethyllolpropane, of 40-tuply ethoxylated glycerol, of 40-tuply ethoxylated trimethylolethane and also of 40-tuply ethoxylated trimethylolpropane.

Very particularly preferred for use as crosslinkers b') are diacrylated, dimethacrylated, triacrylated or trimethacrylated multiply ethoxylated and/or propoxylated glycerols as described for example in prior German patent application DE 10319462.2. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 weight ppm) in the water-absorbing polymer and the aqueous extracts of water-absorbing polymers produced therewith have an almost unchanged surface tension compared with water at the same temperature (typically not less than 0.068 N/m).

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvlnylpyrrolidone, starch, starch derivatives, polyglycols or polyacrylic acids, preferably polyvinyl alcohol and starch.

The reaction can be carried out in the presence of an inert carrier gas, inert meaning that the carrier gas cannot react with the constituents of the monomer solution. The inert carrier gas is preferably nitrogen. The oxygen content of the inert carrier gas is advantageously below 1% by volume, preferably below 0.5% by volume and more preferably below 0.1% by volume.

The inert carrier gas can be passed through the reaction space concurrently with or countercurrently to the free-falling droplets of the monomer solution, preferably cocurrently. Preferably, some or all of the carrier gas, preferably at least 50% of the carrier gas and more preferably at least 75% of the carrier gas is returned into the reaction space as cycle gas after one pass. Typically, some of the carrier gas and preferably at least 10% of the carrier gas is removed from the system after each pass.

The gas velocity is preferably such that the flow in the reactor is laminar in that for example there are no convection eddies opposite to the general direction of flow, and is for example in the range from 0.02 to 1.5 m/s and preferably in the range from 0.05 to 0.4 m/s.

The reaction temperature is preferably in the range from 70 to 250° C., more preferably in the range from 80 to 190° C. and most preferably in the range from 90 to 160° C.

The concentration of monomer a) in the monomer solution is typically in the range from 2% to 80% by weight, preferably in the range from 5% to 70% by weight and more preferably in the range from 10% to 60% by weight.

The solubility of monomer a) in water is typically at least 1 g/100 g of water, preferably at least 5 g/100 g of water, more preferably at least 25 g/100 g of water and most preferably at least 50 g/100 g of water.

Preferred polymerization inhibitors require dissolved oxygen for optimum performance. Therefore, the polymerization inhibitors may be freed of dissolved oxygen prior to polymerization by inertization, i.e., flowing an inert gas, preferably nitrogen, through them. The oxygen content of the monomer solution prior to polymerization is preferably lowered to less than 1 weight ppm and more preferably to less than 0.5 weight ppm.

The monomers are polymerized with each or one another in aqueous solution in the presence of initiators.

The initiators are used in customary amounts, for example in amounts from 0.001% to 5% by weight and preferably from 0.01% to 1% by weight, based on the monomers to be polymerized.

Useful initiators include all compounds which disintegrate into free radicals under the polymerization conditions, examples being peroxides, hydroperoxides, hydrogen peroxide, persulfates, azo compounds and redox initiators. Preference is given to the use of water-soluble initiators. In some cases it is advantageous to use mixtures of various initiators, examples being mixtures of hydrogen peroxide and sodium or potassium peroxodisulfate. Mixtures of hydrogen peroxide and sodium peroxodisulfate can be used in any proportion.

Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristil peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide and tert-aryl perneodecanoate.

Preferred initiators are azo compounds, examples being 2,2'-azobisisobutyronitrile, 2,2'-azobis(2,4-dimethylvaleronitrile) and 2,2'-azobis(4-methoxy-2,4-dimethylvaleronitrile), especially water-soluble azo initiators, examples being 2,2'-azobis{2-[1-(2-hydroxyethyl)-2-imidazolin-2-yl]propane}dihydrochloride, 2,2'-azobis-(2-amidinopropane) dihydrochloride, 2,2'-azobis[2-(2-imidazolin-2-yl)propane] dihydrochloride and 2,2'-azobis[2-(5-methyl-2-imidazolin-2-yl)propane]dihydrochloride. Very particular preference is given to 2,2'-azobis[2-(2-imidazolin-2-yl)propane]dihydrochloride and 2,2'-azobis[2-(5-methyl-2-imidazolin-2-yl)propane]dihydrochloride.

Redox initiators are also further preferred initiators. In redox initiators, the oxidizing component is at least one of the peroxo compounds indicated above and the reducing component is for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide or sodium hydroxymethylsulfoxylate. The reducing component in the redox catalyst is preferably ascorbic acid or sodium pyrosulfite. Based on the amount of monomers used in the polymerization, for example from $1\times10^{-5}$ to 1 mol % is used of the reducing component of the redox catalyst.

It is particularly preferable to induce the polymerization through the action of high energy radiation, in which case it is customary to use photoinitiators as initiator. Useful photoinitiators include for example α-splitters, H-abstracting systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds, such as the free radical formers mentioned above, substituted hexaarylbisimidazoles or acylphosphine oxides, especially 2-hydroxy-2-methylpropiophenone (Darocure® 1173). Examples of azides are 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl-2'-(N,N-dimethylamino)ethyl sulfone, N-(4-sulfonylazidophenyl)maleinimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azido-benzylidene)-4-methylcyclohexanone.

Particularly preferred initiators are azo initiators, such as 2,2'-azobis[2-(2-imidazolin-2-yl)propane]dihydrochloride and 2,2'-azobis[2-(5-methyl-2-imidazolin-2-yl)propane]dihydrochloride, and photoinitiators, such as 2-hydroxy-2-methylpropiophenone and 1-[4-(2-hydroxyethoxy)phenyl]-2-hydroxy-2-methyl-1-propan-1-one, redox initiators, such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and also mixtures thereof.

The pH of the monomer solution is not decisive. But, the pH of the polymer of the pre-sent invention can be adjusted to the desired range, dictated by product requirements, via the pH of the monomer solution. For example, polymers for cosmetic applications should typically have a pH in the range from 5 to 6.

The reaction is preferably carried out in apparatuses which are also suitable for spray drying. Such reactors are described for example in K. Masters, Spray Drying Handbook, 5th Edition, Longman, 1991, pages 23 to 66.

One or more spray nozzles can be used in the process of the invention. Usable spray nozzles are not subject to any restriction. The liquid to be spray dispensed may be fed to such nozzles under pressure. The atomizing of the liquid to be spray dispensed may in this case be effected by decompressing the liquid in the nozzle bore after the liquid has reached a certain minimum velocity. Also useful for the purposes of the present invention are one-material nozzles, for example slot nozzles or swirl or whirl chambers (full cone nozzles, available for example from Düsen-Schlick GmbH, Germany, or from Spraying Systems Deutschland GmbH, Germany).

Preference for the purposes of the present invention is given to full cone nozzles. Of these, those having a spray cone opening angle in the range from 60 to 180° are preferred and those having an opening angle in the range from 90 to 120° are particularly preferred. For the purposes of the present invention, the average droplet diameter which results on spraying is typically less than 1000 μm, preferably less than 200 μm, more preferably less than 100 μm and customarily greater than 10 μm, preferably greater than 20 μm and more preferably greater than 50 µm, and can be determined by customary methods, such as light scattering, or by reference to the characteristic curves available from nozzle makers. The throughput per spray nozzle is advantageously in the range from 0.1 to 10 m³/h and frequently in the range from 0.5 to 5 m³/h.

The droplet diameter resulting in the course of spraying is advantageously in the range from 10 to 1000 µm, preferably in the range from 10 to 500 µm, more preferably in the range from 10 to 150 µm and most preferably in the range from 10 to 45 µm.

The reaction can also be carried out in apparatuses in which the monomer solution can free fall in the form of monodisperse droplets. Suitable for this purpose are apparatuses as described for example in U.S. Pat. No. 5,269,980 column 3 lines 25 to 32.

Dropletization through laminar jet disintegration as described in Rev. Sci. Instr., volume 38 (1966), pages 502 to 506 is likewise possible.

Dropletization is preferred to spraying, in particular when photoinitiators are used. Dropletization in the process of the present invention provides polymeric thickeners having a low fraction of dust, and optimum bulk density and good flowability.

If, however, high throughputs of monomer solution are desired, spraying of the monomer solution into the reaction space is preferred.

The reaction space of the polymerization reactor can be carried out in overpressure or in underpressure, an underpressure of up to 100 mbar below ambient being preferred.

The polymerization rate and the drying rate typically have different temperature dependencies. This can mean, for example, that the sprayed droplets dry before the desired conversion has been achieved. It is therefore advantageous to control the reaction rate and the drying rate separately.

The drying rate can be controlled via the water vapor content of the inert gas. The water vapor content of the inert gas is generally up to 90% by volume and preferably up to 50% by volume.

The polymerization rate can be controlled through the identity and amount of the initiator system used.

The use of azo compounds or redox initiators as initiators is advantageous for directing the rate of polymerization. The starting characteristics of the polymerization are better directable with azo compounds or redox initiators via the choice of initiator, initiator concentration and reaction temperature than for example with pure peroxide initiators.

Photoinitiators are particularly advantageous. When photoinitiators are used, the drying rate can be controlled to the desired value via the temperature without thereby significantly influencing the free-radical formation process at the same time.

The carrier gas is advantageously preheated to the reaction temperature of 70 to 250° C., preferably 80 to 190° C. and more preferably 90 to 160° C. upstream of the reactor.

The reaction offgas, i.e., the carrier gas leaving the reaction space, can be cooled down in a heat exchanger for example. Water and unconverted monomer condense in the process. Thereafter, the reaction offgas can be at least partially reheated and returned into the reactor as recycle gas. Preferably, the recycle gas is cooled down such that the cooled recycle gas has the water vapor fraction desired for the reaction. A portion of the reaction offgas can be removed from the system and replaced by fresh carrier gas, in which case unconverted monomers comprised in the reaction offgas can be separated off and recycled.

Particular preference is given to an integrated energy system whereby a portion of the heat rejected in the cooling of the offgas is used to heat up the cycle gas.

The reactors can be trace heated. Any trace heating is adjusted such that the wall temperature is not less than 5° C. above reactor internal temperature and condensation at reactor walls is reliably avoided.

The reaction product can be removed from the reactor in a conventional manner, preferably at the base via a conveying screw, and if appropriate be further dried to the desired residual moisture content and to the desired residual monomer content, for example in an integrated fluidized bed.

The present invention further provides the water-absorbing polymeric particles obtainable by the process of the present invention.

The present invention further provides water-absorbing polymeric particles comprising
i) at least one polymerized ethylenically unsaturated acid-functional monomer which, if appropriate, may be at least partially neutralized,
ii) at least one polymerized crosslinker,
iii) if appropriate one or more polymerized ethylenically and/or allylically unsaturated monomers copolymerizable with the monomers identified under i), and
iv) if appropriate one or more water-soluble polymers onto which the monomers identified under i) are at least partly grafted,
wherein the concentration of the polymerized crosslinker ii) is higher in the region of the particle surface than in the particle interior and wherein the remarks made above in relation to the components a) to d) apply mutatis mutandis to the components i) to iv).

The increased density of crosslinking in the region of the particle surface is achieved without any additional post-crosslinking step. Of course, the water-absorbing polymeric particles obtainable by the process of the present invention can be additionally postcrosslinked, if necessary.

The increased density of crosslinking in the region of the particle surface is characterized by a high Centrifuge Retention Capacity (CRC) and a high Absorbency Under Load (AUL) for the water-absorbing polymeric particles.

The water-absorbing polymeric particles of the present invention typically have a Centrifuge Retention Capacity (CRC) of at least 15 g/g, preferably at least 20 g/g and more preferably at least 25 g/g. Centrifuge Retention Capacity (CRC) is determined by EDANA (European Disposables and Nonwovens Association) recommended test method No. 441.2-02 "Centrifuge retention capacity".

The water-absorbing polymeric particles of the present invention typically have an absorbency under load 0.3 psi (2.07 kPa) of at least 10 g/g, preferably at least 15 g/g and more preferably at least 20 g/g. Absorbency Under Load (AUL) is determined by EDANA (European Disposables and Nonwovens Association) recommended test method No. 442.2-02 "Absorption under pressure".

The present invention further provides processes for producing hygiene articles, in particular diapers, comprising the use of water-absorbing polymeric particles produced by the process of the present invention.

The present invention further provides hygiene articles comprising an absorbent layer comprising from 50% to 100% by weight, preferably from 60% to 100% by weight, more preferably from 70% to 100% by weight, even more preferably from 80% to 100% by weight and most preferably from 90% to 100% by weight of water-absorbing polymeric particles according to the present invention, the envelope surrounding the absorbent layer not included of course.

To determine the quality of postcrosslinking, the dried water-absorbing polymeric particles are tested using the test methods described hereinbelow.

Methods:

The measurements should be carried out, unless otherwise stated, at an ambient temperature of 23±2° C. and a relative humidity of 50±10%. The water-absorbing polymeric particles are thoroughly mixed through before measurement.

Centrifuge Retention Capacity (CRC)

Centrifuge Retention Capacity of the water-absorbing polymeric particles is determined by EDANA (European Disposables and Nonwovens Association) recommended test method No. 441.2-02 "Centrifuge retention capacity".

Absorbency Under Load (AUL)

Absorbency Under Load of the water-absorbing polymeric particles is determined by EDANA (European Disposables and Nonwovens Association) recommended test method No. 442.2-02 "Absorption under pressure".

Extractables

The level of extractable constituents in the water-absorbing polymeric particles is determined by EDANA (European Disposables and Nonwovens Association) recommended test method No. 470.2-02 "Determination of extractable polymer content by potentiometric titration".

Residual Monomers

The level of residual monomers in the water-absorbing polymeric particles is determined by EDANA (European Disposables and Nonwovens Association) recommended test method No. 410.2-02 "Residual monomers".

Median Particle Size

The median size of the water-absorbing polymeric particles is determined by EDANA (European Disposables and Nonwovens Association) recommended test method No. 420.2-02 "Particle size distribution".

The EDANA test methods are obtainable for example at European Disposables and Nonwovens Association, Avenue Eugéne Plasky 157, B-1030 Brussels, Belgium.

EXAMPLES

Example 1

300 g of a PO/EO block polymer, 12.9 g of acrylic acid, 0.3 g of hydroquinone monomethyl ether, 0.09 g of copper(II) chloride, 0.3 g of hypophosphorous acid, 0.1 g of triphenyl phosphite, 300 g of cyclohexane and 4.5 g of sulfuric acid were charged to a round bottom flask equipped with a Dean & Stark apparatus. A total of 7 ml of water were removed at a reaction temperature of about 82° C. in the course of 8 hours. Cyclohexane was subsequently distilled off. The crosslinker A was not further purified.

Crosslinker A is the diacrylate of a block polymer of propylene oxide and ethylene oxide (general formula II where R=hydrogen, B=propylene glycol, C=carbonyl, y=about 15 and x+z=about 2).

Example 2

300 g of a PO/EO block polymer, 7.4 g of acrylic acid, 0.3 g of hydroquinone monomethyl ether, 0.09 g of copper(II) chloride, 0.3 g of hypophosphorous acid, 0.1 g of triphenyl phosphite, 300 g of cyclohexane and 4.5 g of sulfuric acid were charged to a round bottom flask equipped with a Dean & Stark apparatus. A total of 6 ml of water were removed at a reaction temperature of about 82° C. in the course of 8 hours. Cyclohexane was subsequently distilled off. The crosslinker B was not further purified.

Crosslinker B is the diacrylate of a block polymer of propylene oxide and ethylene oxide (general formula II where R=hydrogen, B=propylene glycol, C=carbonyl, y=about 19 and x+z=about 11).

Example 3

300 g of a PO/EO block polymer, 3.1 g of acrylic acid, 0.3 g of hydroquinone monomethyl ether, 0.09 g of copper(II) chloride, 0.3 g of hypophosphorous acid, 0.1 g of triphenyl phosphite, 300 g of cyclohexane and 4.5 g of sulfuric acid were charged to a round bottom flask equipped with a Dean & Stark apparatus. A total of 3 ml of water were removed at a reaction temperature of about 82° C. in the course of 6 hours. Cyclohexane was subsequently distilled off. The crosslinker C was not further purified.

Crosslinker C is the diacrylate of a block polymer of propylene oxide and ethylene oxide (general formula II where R=hydrogen, B=propylene glycol, C=carbonyl, y=about 30 and x+z=about 27).

Examples 4 to 8

A solution comprising 25.2 kg of acrylic acid, 16.6 kg of 50% aqueous sodium hydroxide solution, 220 or 255 g of crosslinker or crosslinker mixture respectively, 55 kg of water and 1.8 kg of 2,2'-azobis(N,N'-dimethyleneisobutyramidine) dihydrochloride (Azoinitiator V44 from Wako Deutschland, Germany) was dropletized or jetted in a heated spray tower (150° C., 12 m high, 2 m wide, filled with nitrogen atmosphere) cocurrently at a gas velocity of 0.1 m/s. A dry, white powder was obtained at the base of the spray tower.

The experimental conditions and the experimental results are summarized in the tables which follow:

TABLE 1

| | Experimental conditions | | |
|---|---|---|---|
| Example | Crosslinker 1 | Crosslinker 2 | Metering |
| 4 | 0.22% by weight of PEGDA 400 | | dropletized through 150 μm hole |
| 5 | 0.15% by weight of PEGDA 400 | 0.10% by weight of crosslinker A from Example 1 | dropletized through 150 μm hole |
| 6 | 0.15% by weight of PEGDA 400 | 0.10% by weight of crosslinker B from Example 2 | dropletized through 150 μm hole |
| 7 | 0.15% by weight of PEGDA 400 | 0.10% by weight of crosslinker C from Example 3 | dropletized through 150 μm hole |
| 8 | 0.15% by weight of PEGDA 400 | 0.10% by weight of crosslinker A from Example 1 | jetted through 400 μm hole |

PEGDA 400 is the diacrylate of a polyethylene glycol having an average molar mass of about 400 g/mol.
The weight percentages are based on total solution.

TABLE 2

| Example | Extractables | Residual monomer | CRC | AUL 0.3 psi | Median particle size |
|---|---|---|---|---|---|
| 4 | 18.2% | 1.5% by weight | 19.1 g/g | 9.2 g/g | 220 μm |
| 5 | 19.0% | 1.2% by weight | 22.5 g/g | 18.1 g/g | 218 μm |
| 6 | 17.5% | 1.4% by weight | 21.2 g/g | 17.6 g/g | 210 μm |
| 7 | 18.0% | 1.5% by weight | 20.3 g/g | 16.8 g/g | 235 μm |
| 8 | 22.0% | 1.7% by weight | 15.5 g/g | 14.6 g/g | 80 μm |

We claim:

1. A process for producing water-absorbing polymeric particles by spray polymerization of a monomer solution comprising
spray dispensing a monomer solution comprising
a) at least one ethylenically unsaturated acid-functional monomer,
b) at least one crosslinker of formula

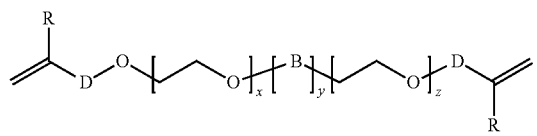

wherein
R represents the same or different radicals selected from the group consisting of hydrogen, methyl, and ethyl,
B represents the same or different groups selected from

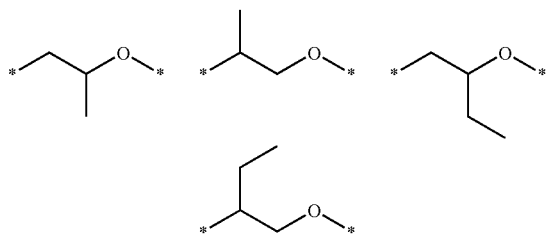

and * designates the positions of attachment,
D represents the same or different groups selected from carbonyl and methylene,
x and z are the same or different and each represents an integer from 2 to 30, and
y represents an integer from 5 to 60,
wherein the crosslinker b) equilibrates in the monomer solution in less than 10 seconds in an ASTM D3825 measurement of dynamic surface tension,
b') a crosslinker having at least two free-radical polymerizable groups for crosslinking the polymeric particle interior;
c) optionally one or more ethylenically and/or allylically unsaturated monomers copolymerizable with the monomer a), and
d) optionally one or more water-soluble polymers onto which the monomers a), b) and c) can be at least partly grafted,
to form droplets of the monomer solution, wherein the at least one crosslinker b) accumulates at the droplet surface; and
polymerizing the droplets of the monomer solution to form the water-absorbing polymeric particles.

2. The process according to claim 1 wherein the monomer a) is acrylic acid or methacrylic acid.

3. The process according to claim 1 wherein the monomer a) is partially neutralized acrylic acid or methacrylic acid.

4. The process according to claim 1 wherein the water-absorbing polymeric particles consist essentially of polymerized and unpolymerized components a), b), b'), c), and d) of the monomer solution.

5. The process according to claim 1 wherein the water-absorbing polymeric particles consist essentially of polymerized and unpolymerized components a), b), b'), c), and d) of the monomer solution.

6. The process according to claim 1 wherein b') is selected from the group consisting of ethylene glycol dimethacrylate, diethylene glycol diacrylate, allyl methacrylate, trimethylolpropane triacrylate, triallylamine, tetraallyloxyethane, N,N'-methylenebisacrylamide, N,N'-methylenebismethacrylamide, butanediol diacrylate, butanediol dimethacrylate, trimethylolpropane triacrylate, allyl(meth)acrylate, triallyl cyanurate, diallyl maleate, a polyallyl ester, tetraallylethylenediamine, pentaerythritol diallyl ether, pentaerthyritol triallyl ether, pentaerythritol tetrallyl ether, polyethylene glycol diallyl ether, ethylene glycol diallyl ether, glycerol diallyl ether, glycerol triallyl ether, di- and triacrylates of 3- to 15-tuply ethoxylated glycerol, di- and tri-acrylates of 3- to 15-tuply ethoxylated trimethylolpropane, and di- and tri-acrylates of 3- to 15-tuply ethoxylated trimethylolethane.

* * * * *